United States Patent [19]
Skottun

[11] Patent Number: 6,048,364
[45] Date of Patent: Apr. 11, 2000

[54] HIGHLY DEFORMABLE INTRAOCULAR LENS AND METHOD FOR INSERTING SAME INTO AN EYE

[76] Inventor: Bernt Christian Skottun, 273 Mather St., Piedmont, Calif. 94611-5154

[21] Appl. No.: 09/100,513

[22] Filed: Jun. 20, 1998

[51] Int. Cl.[7] .................................................. A61F 2/16
[52] U.S. Cl. ................................................................ 623/6
[58] Field of Search .......................... 623/6; 606/107–166

[56] References Cited

U.S. PATENT DOCUMENTS

| | | |
|---|---|---|
| 4,373,218 | 2/1983 | Shachar . |
| 4,585,457 | 4/1986 | Kalb . |
| 4,731,078 | 3/1988 | Stoy et al. ................................... 623/6 |
| 4,822,360 | 4/1989 | Deakon . |
| 4,932,966 | 6/1990 | Christie et al. ............................. 623/6 |
| 4,995,880 | 2/1991 | Galib ........................................... 623/6 |
| 5,026,396 | 6/1991 | Darin ........................................... 623/6 |
| 5,035,710 | 7/1991 | Nakada et al. . |
| 5,158,572 | 10/1992 | Nielsen ....................................... 623/6 |
| 5,213,579 | 5/1993 | Yamada et al. . |
| 5,728,155 | 3/1998 | Anello et al. ............................... 623/6 |

OTHER PUBLICATIONS

Kessler, J. (1964) Experiments in refilling the lens. Archives of Ophthalmology, vol. 71, pp. 412–417.

Nishi et al. (1989) Further development of experimental techniques for refilling the lens of animal eyes with a balloon. J. Catarct Refract. Surge., vol. 15, pp. 584–588.

*Primary Examiner*—David H. Willse
*Assistant Examiner*—Suzette Jackson

[57] ABSTRACT

An intraocular lens which can be deformed substantially so as to be inserted through a very small incision in the eye. The intraocular lens has an optical element (10) made from a flexible membrane (18) and is filled with a fluid optical medium. Attached to the optical element is a bladder (12) into which the fluid medium from the optical element (10) can be shunted. When inserting the intraocular lens the fluid medium is first shunted from the optical element (10) into the bladder (12); this reduces the size of the optical element (10). With the optical element (10) in this state of reduced size it is passed through the cornea through a small incision. With the optical element (10) now inside the eye and the bladder (12) outside the eye, the fluid medium is shunted back from the bladder (12) into the optical element (10). This reduces the size of the bladder (12) allowing also it to be passed through the small incision. In this way the whole intraocular lens is passed into the eye through a small incision.

13 Claims, 7 Drawing Sheets

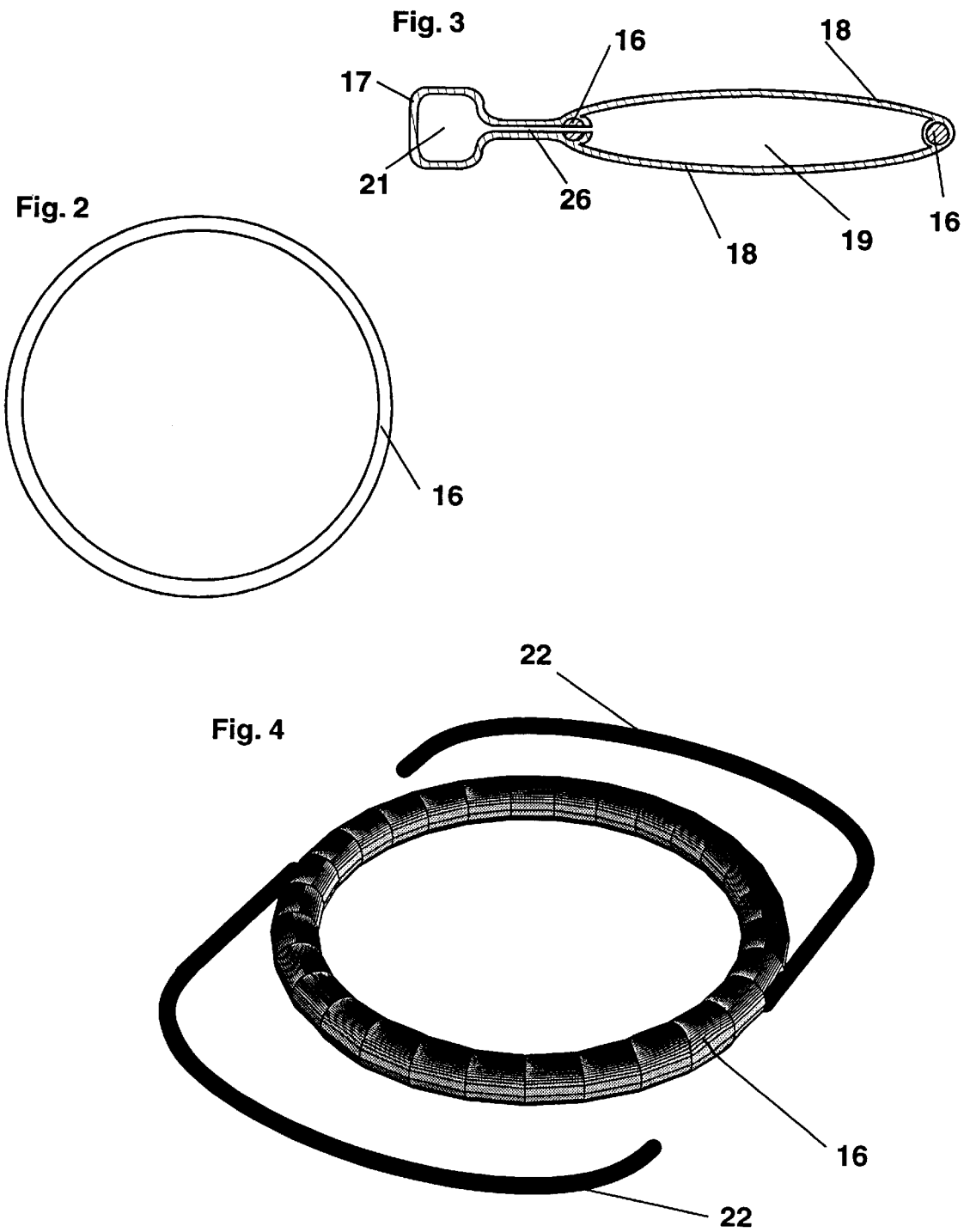

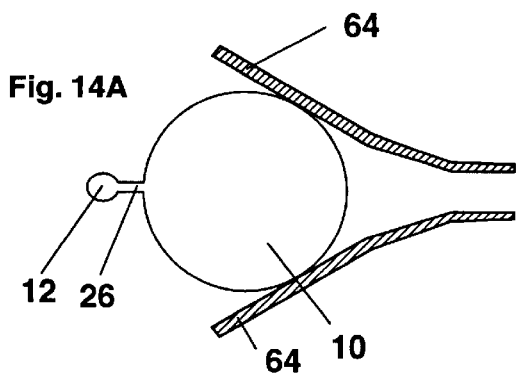
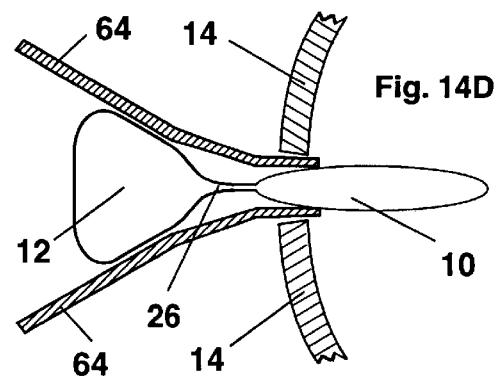
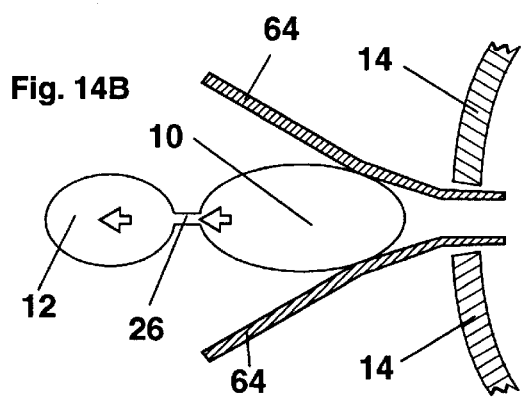
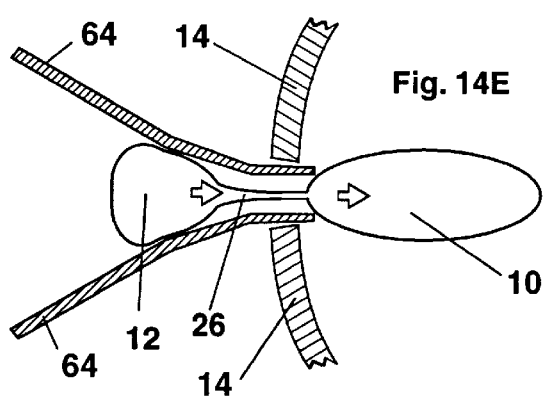
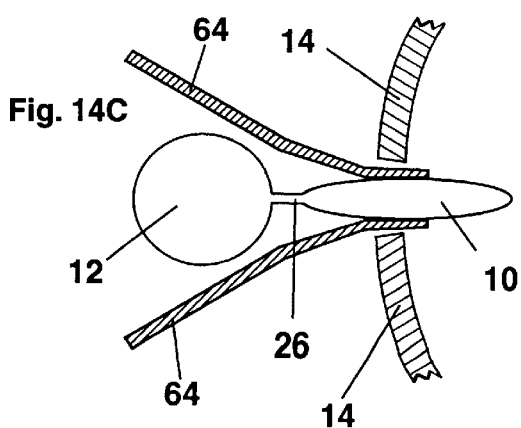
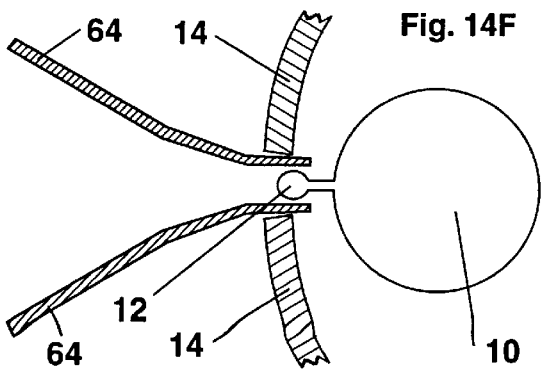

HIGHLY DEFORMABLE INTRAOCULAR LENS AND METHOD FOR INSERTING SAME INTO AN EYE

BACKGROUND—FIELD OF INVENTION

This invention relates to intraocular lenses, specifically to such intraocular lenses as can be inserted into an eye through a small incision.

BACKGROUND—DESCRIPTION OF PRIOR ART

Cataract surgery typically involves removing the cataractous natural lens and replacing it with an artificial intraocular lens. The surgery is most commonly performed by making an incision in the cornea. An adverse consequence of this incision is that patients commonly are left with some degree of postoperative astigmatism. The amount of astigmatism appears to be directly related to the size of the incision: the larger the incision the more astigmatism. This has made it highly desireable to reduce the size of corneal incisions.

Using phacoemulsification, in which the natural lens is emulsified with ultrasound and extracted with suction, it is possible to extract the cataractous lens through a very small opening in the eye. Currently the limiting factor, as far as incision size is concerned, is the space required for inserting the replacement intraocular lens into the eye. In order to have sufficient optical power conventional intraocular lenses need to occupy a certain volume. This volume is what determines the size of the corneal incision.

A number of procedures and techniques have been proposed for reducing the size of the intraocular lens at the time of implantation. These involve folding and rolling the intraocular lens then unfolding or unrolling it once inside the eye. Folding is currently in wide-spread use. The main problem with folding is that how much the cross section of an intraocular can be reduced by folding is highly limited. Currently, the size of incisions required for implantation of these kinds of intraocular lenses are on the order of 4 millimeters. Passing folded intraocular lenses through incisions substantially smaller than that has proved to be very difficult.

Other techniques for reducing the size of the intraocular lens at the time of implantation have been proposed. It has been suggested that one could use Fresnel lenses. Fresnel lenses, which are flat, could be rolled and then unrolled inside the eye. A problem with Fresnel lenses is that they carry with them a substantial amount of optical distortion. Another suggestion is to insert an intraocular lens, in the form of an empty balloon, into the emptied lens capsule and once in place use a syringe to fill it with an fluid optical medium. The problem with this proposal is that it requires some way of safely and effectively sealing the opening in the balloon. If the contents of the balloon were to escape out of the intraocular lens, then it could easily make its way to the anterior chamber of the eye, where it could block the outflow of aqueous from the eye and cause glaucoma. This would be a very dangerous situation. The problem of leakage is made more probable and serious by the fact that a not insignificant amount of pressure may have to be applied to the interior of the balloon in order to make it assume the appropriate shape for acting as a lens.

A further and more ambitious procedure involving the filling of structures inside the eye is Phaco-Ersatz in which the cataractous lens is extracted using phaco-emulsification through a very small opening in the lens capsule. The lens capsule, which is left intact, is then filled with a replacement medium. This technique carries with it the same problem of safety as the balloon technique described above. In addition, Phaco-Ersatz has the further problem that it requires the lens capsule to be in very good condition, because it is the capsule which will provide the new lens with its shape.

From the perspective of being able to insert an intraocular lens through a small corneal incision, the currently available intraocular lenses and the hitherto proposed intraocular lenses have a number of disadvantages:

(a) The extent to which the cross section of the intraocular lens can be reduced is highly limited.
(b) The intraocular lens can be difficult to implant.
(c) In the case of Fresnel lenses there are severe optical distortions.
(d) Methods which involve in situ filling of some hollow structure carry with them a danger of creating glaucoma.
(e) In the case of Phaco-Ersatz the lens capsule has to be in extremely good condition.

ADVANTAGES

Several advantages of the present invention are:

(a) to provide an intraocular lens which can be inserted through a very small opening in the eye;
(b) to be simple to insert so as to not require exceptional skills on the part of the surgeon;
(c) to avoid severe optical distortions;
(d) to be safe, and
(e) to tolerate a reasonable amount of damage to the lens capsule as result of lens extraction.

Further advantages will become apparent from a consideration of the ensuing description and drawings.

DRAWING—FIGURES

FIG. 2 shows a frontal view of a structural ring which may be used as a structural element for the highly deformable intraocular lens.

FIG. 3 shows a cross section through the highly deformable intraocular lens.

FIG. 4 shows a perspective drawing of the structural ring to which have been attached a pair of haptics.

FIGS. 14A to 14F show in cross section how the highly deformable intraocular lens may be inserted through a very small opening in the cornea using a funnel-shaped insertion tool.

REFERENCE NUMERALS IN DRAWINGS

Figure 1A:
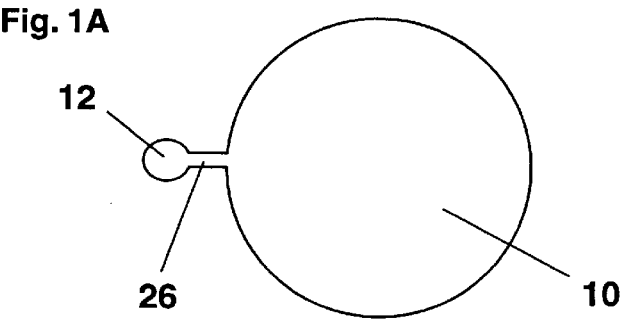
FIGS. 1A to 1E show schematically, in frontal view, the insertion into the eye of the highly deformable intraocular lens.

| | |
|---|---|
| 10 optical element | 12 bladder |
| 14 cornea | 16 structural ring |
| 17 membrane of bladder | 18 flexible membrane |
| 19 internal cavity of optical element | |
| 21 internal cavity of bladder | |
| 22 haptic | 24 corneal incision |
| 26 duct | 28 valve |
| 30 cross bar | 32 side bar |
| 34 lip | 36 strut |
| 40 blade | 42 handle |
| 44 opening | 46 projection |
| 50 rivet | 52 right half of tool |
| 54 left half of tool | 56 internal membrane |
| 58 small internal compartment | |
| 59 major internal space | 64 funnel-shaped insertion tool |
| 70 lumen | 80 tube |
| 82 large opening | 84 small opening |
| 86 notch | 90 plunger |
| 92 spring loaded blade | |

Description

The basic principle behind the highly deformable intraocular lens and the method of inserting it into a human eye through a small corneal incision 24 is shown in FIG. 1A through FIG. 1E. Corneal incision 24 forms an opening in a cornea 14 through which it is possible to pass small objects to the interior of the eye.

The highly deformable intraocular lens system includes an optical element 10 and a bladder 12. Optical element 10 is hollow and contains an internal cavity 19 of optical element. Also bladder 12 is hollow and comprises an internal cavity 21 of bladder. Bladder 12 is separated from optical element 10. Optical element 10 and bladder 12 are filled with a fluid medium having a refractive index higher than that of the aqueous humor. Internal cavity of optical element 19 communicates with internal cavity of bladder 21 through a duct 26 which allows the fluid medium to be shunted between optical element 10 and bladder 12. Both optical element 10 and bladder 12 are made from resilient materials allowing them to change their respective volumes as the fluid medium is redistributed between them. Together optical element 10, bladder 12, and duct 26 form a closed system.

Figure 1B:
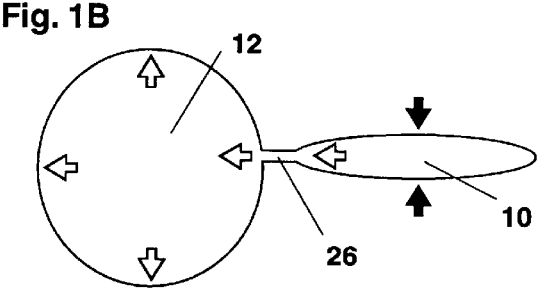
Figure 1D:
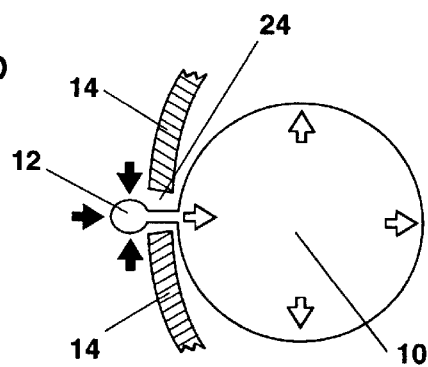
Figure 1C:
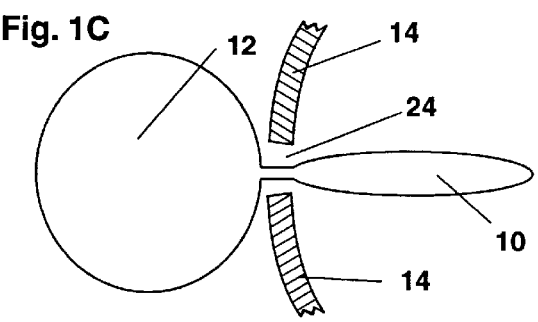
Figure 1E:
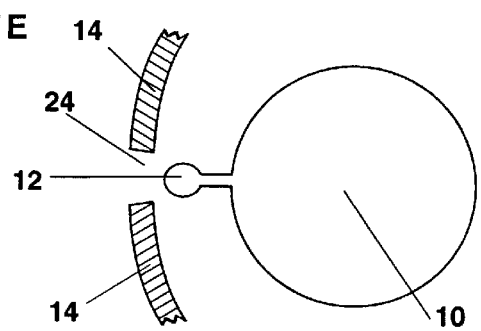

FIGS. 1A, 1D and 1E show optical element 10 in its fully un-compressed state. That optical element 10 is un-compressed is indicated by its circular outline when seen from the front. In FIGS. 1B and 1C optical element 10 has been compressed. The outline of optical element 10 is now that of a narrow ellipse. FIGS. 1A to 1E show the highly deformable intraocular lens from the front.

FIG. 2 shows a structural ring 16 from the front. Structural ring 16 is made from a resilient material allowing it to be deformed in response to application of substantial external forces while retaining the ability to resume its original annular shape once the external forces are no longer being exerted.

FIG. 3 shows a cross section through optical element 10 and bladder 12 demonstrating how structural ring 16 forms the structural support for two transparent flexible membranes 18 which form the front and rear optical surfaces of optical element 10 so as to create internal cavity of optical element 19 in which can be placed a fluid medium. Positive internal pressure in internal cavity of optical element 19 gives flexible membranes 18 spherical shapes allowing optical element 10 to act as a lens. FIG. 3 also shows how an elastic and resilient membrane 17 forms the outer surface of bladder 12 in such a manner as to create an internal cavity of bladder 21. Also shown in FIG. 3 is duct 26 which allows internal cavity of bladder 21 to communicate with internal cavity of optical element 19.

FIG. 4 shows a pair of haptics 22 attached to structural ring 16. Haptics 22 serve as means for attaching the highly deformable intraocular lens to structures inside the eye.

Figure 5:
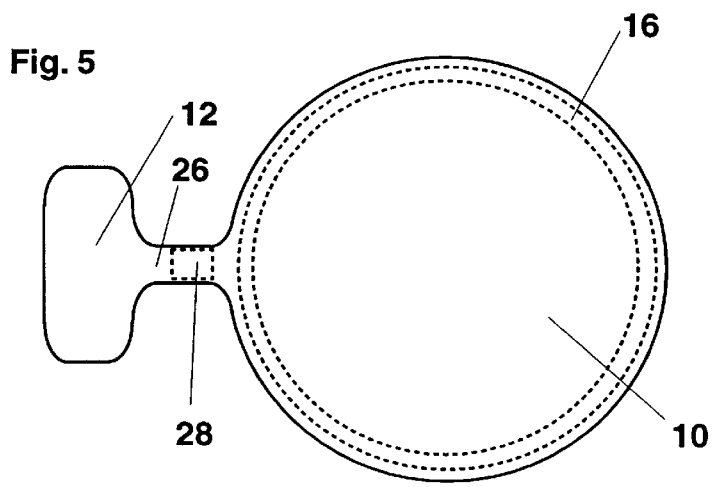
FIG. 5 shows the placement of a valve in the duct connecting the optical element with the bladder and the placing of a structural ring in the optical element.

FIG. 5 depicts the highly deformable intraocular lens in a frontal view and shows the placement of a valve 28 in duct 26 and the placement of structural ring 16 in optical element 10.

Figure 6:
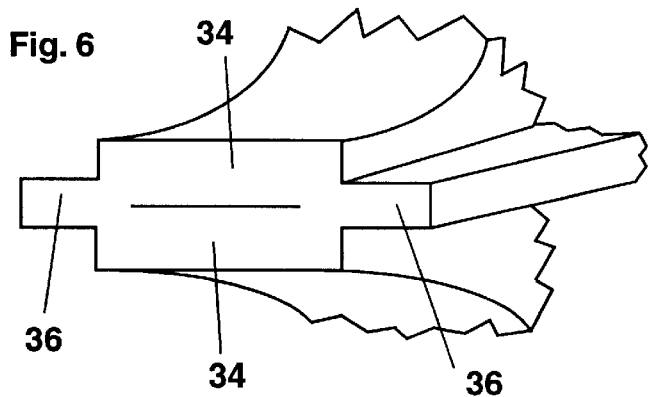
FIG. 6 shows a perspective drawing of the valve in the closed state.
Figure 7:
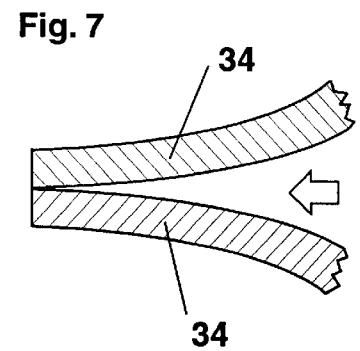
FIG. 7 shows a cross section through the valve in the closed state.
Figure 8:
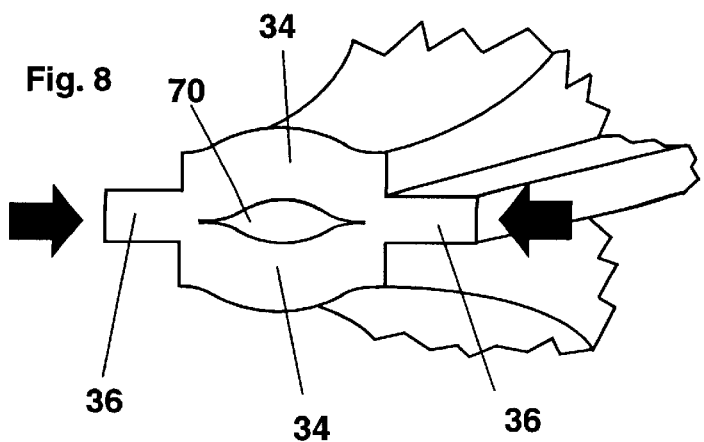
FIG. 8 shows a perspective drawing of the valve in the open state.
Figure 9:
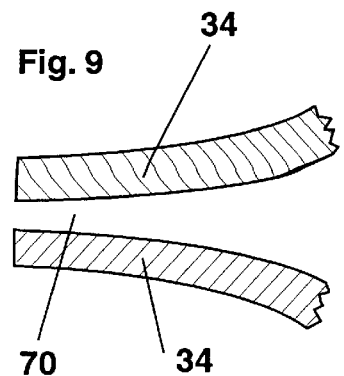
FIG. 9 shows a cross section through the valve in the open state.

FIG. 6 shows an example of valve 28 which can be used to control the flow of fluid medium through duct 26. Valve 28 in its preferred embodiment comprises two essentially parallel lips 34 to which are attached two struts 36. FIG. 6 shows a perspective drawing of valve 28 in the closed condition. FIG. 7 shows a cross section through lips 34 when valve 28 is closed. FIG. 8 shows a perspective drawing of valve 28 in the open condition. The two solid arrows signify pressure which is being applied to struts 36 to open valve 28. As can be seen, in the open condition lips 34 are being made to bend away from each other so as to create an open lumen 70 between them. FIG. 9 shows a cross section through lips 34 when valve 28 is open.

Figure 10:
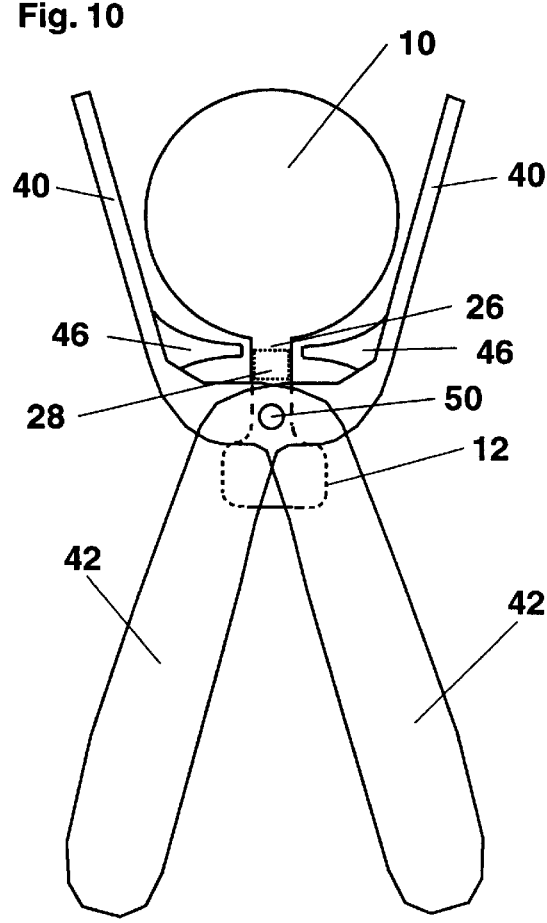
FIG. 10 shows a frontal view of the compression and insertion tool and its relation to the highly deformable intraocular lens prior to any compression of the lens.
Figure 11:
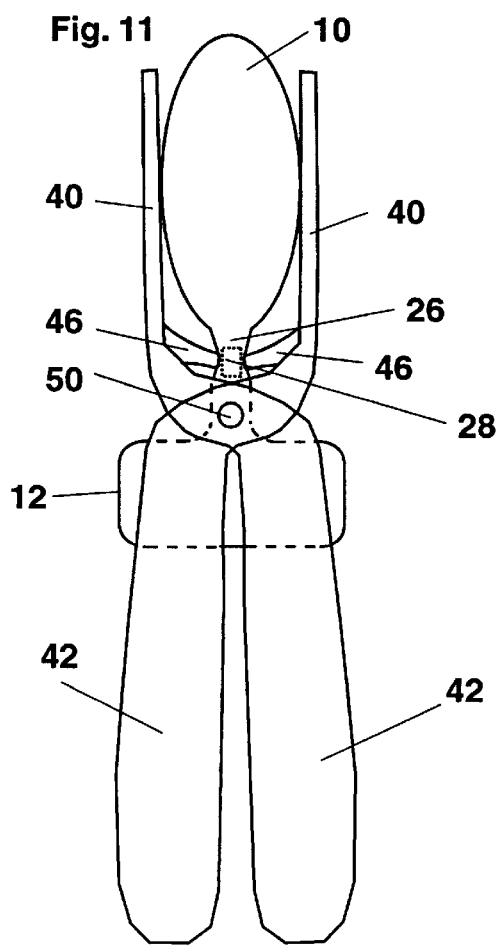
FIG. 11 shows the compression and insertion tool as it compresses the highly deformable intraocular lens.

FIGS. 10 and 11 show a compression and insertion tool which may be used to deform the highly deformable intraocular lens and, once deformed, pass the intraocular lens into the eye of a patient. The compression and insertion tool comprises a pair of blades 40 and a pair of handles 42. Each blade 40 is connected with one handle 42. The structure made up of one blade 40 and one handle 42 is connected to the other structure, which is made up of the other blade 40 and other handle 42, with two rivets 50 allowing the two structures to pivot. Attached to each blade-and-handle structure is a projection 46. FIG. 10 shows the compression and insertion tool in the open position, that is to say without exerting any pressure on the intraocular lens. In FIG. 11 the compression and insertion tool has been closed causing optic element 10 to be compressed into an elliptical shape and shunting the fluid medium from optical element 10 into bladder 12 causing bladder 12 to expand. When the compression and injection tool is in the closed position projections 46 apply pressure on valve 28 situated in duct 26. This pressure serves to open valve 28.

Figure 12:
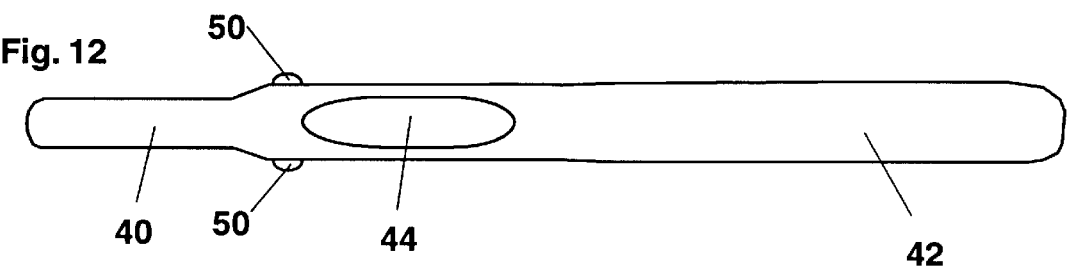
FIG. 12 shows a side view of the compression and insertion tool.

FIG. 12 shows a side view of the compression and insertion tool. From this angle an opening 44 in the side of the compression and insertion tool is evident. Opening 44 is provided in order to allow bladder 12 to protrude through the side of the compression and insertion tool as bladder 12 expands in response to the compression of optical element 10.

Figure 13:
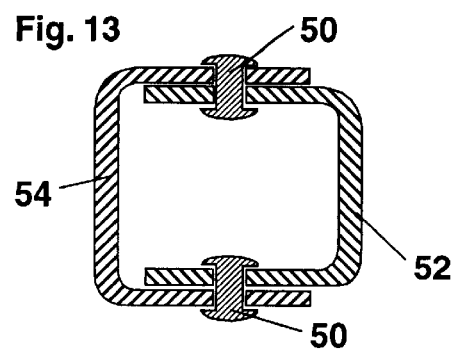
FIG. 13 shows a cross section through the compression and insertion tool at the location where the two halves of the tool are connected to each other with rivets.

FIG. 13 shows a cross section through the compression and insertion tool at the point where the two parts of the tool are connected to each other and around which they are free to pivot. FIG. 13 shows the positioning of rivets 50 and of the right half of tool 52 and the left half of tool 54. The main purpose of this figure is to show that the compression and insertion tool has an open space at its center. This space is provided so as to provide room for duct 26 and to allow bladder 12 to slide out of the compression and insertion tool after the size of bladder 12 has been reduced as a result of shifting fluid medium back into optical element 10.

FIGS. 14A to 14F show cross sections through a funnel-shaped insertion tool 64, and illustrate the process of inserting the highly deformable intraocular lens into an eye using this insertion tool.

Figure 15:
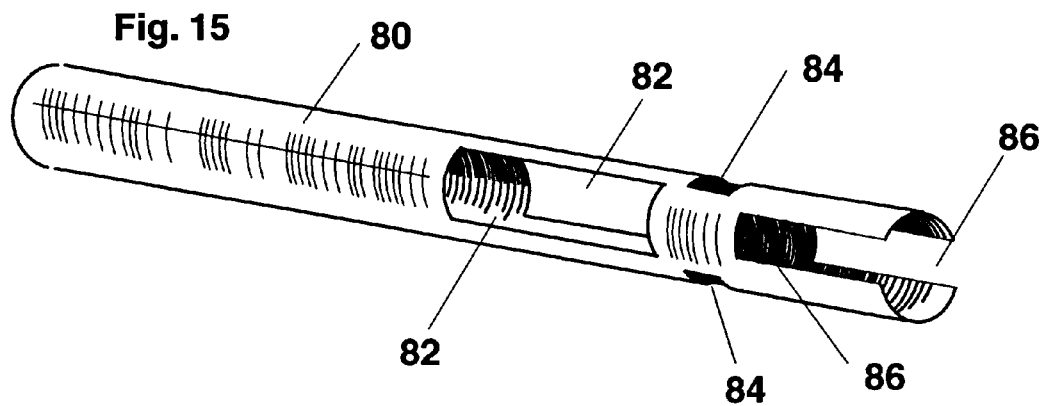
FIG. 15 shows a perspective drawing of a tubular insertion tool.
Figure 16:
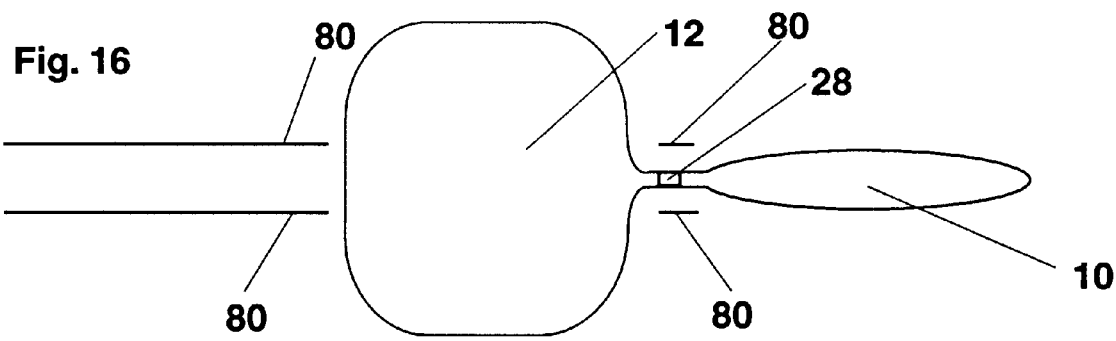
FIG. 16 shows a horizontal cross section through the tubular insertion tool with the highly deformable intraocular lens in it.
Figure 17:
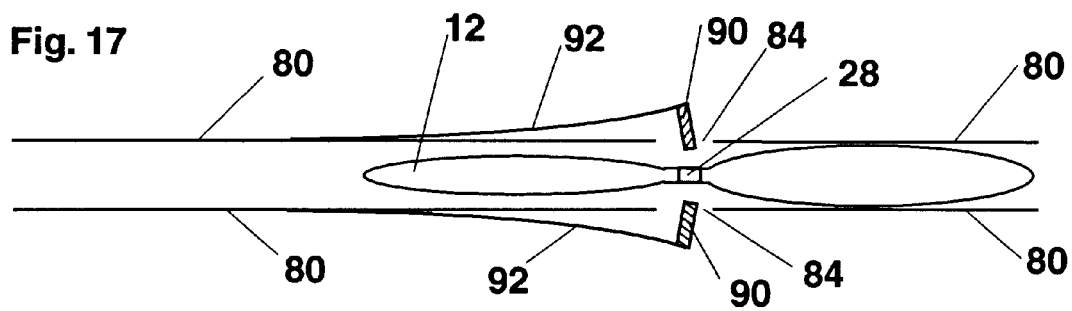
FIG. 17 shows a vertical cross section through the tubular insertion tool which has been fitted with plungers attached to spring loaded blades for exerting pressure on the valve in the duct connecting the bladder and the optical element.
Figure 18:
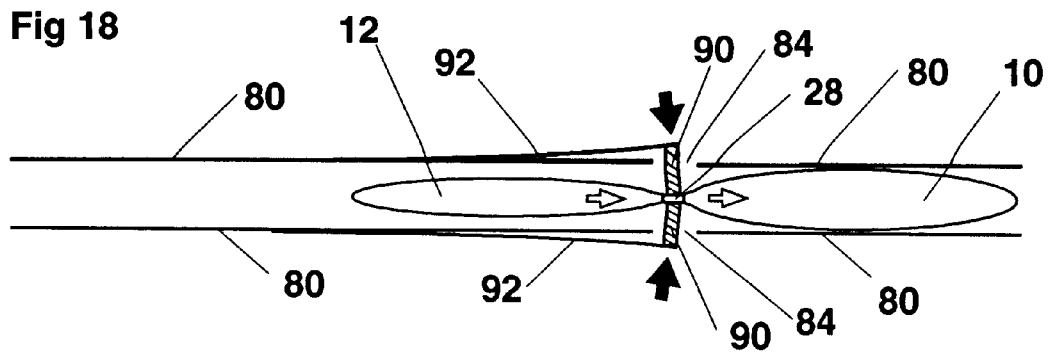
FIG. 18 shows a vertical cross section of the tubular insertion tool in which the plungers have been compressed so as to open the valve allowing fluid to move from the bladder into the optical element.

FIG. 15 shows an insertion tool for use with a pre-compressed intraocular lens. It comprises a tube 80 in which have been made two large openings 82, two small openings 84, and a pair of notches 86. FIGS. 16 and 17 show, respectively, a horizontal and a vertical cross section of the insertion tool. In FIGS. 17 and 18 the insertion tool has been fitted with a pair of plungers 90 each attached to a resilient spring-loaded blade 92. FIG. 18 depicts the same as does FIG. 17 with the exception that spring loaded blades 92 have been compressed in order to bring the attached plungers 90 in direct contact with valve 28 so as to apply outside pressure onto valve 28 causing it to open. The movements of plungers 90 and spring loaded blades 92 are indicated with filled arrows in FIG. 18.

Figure 19:
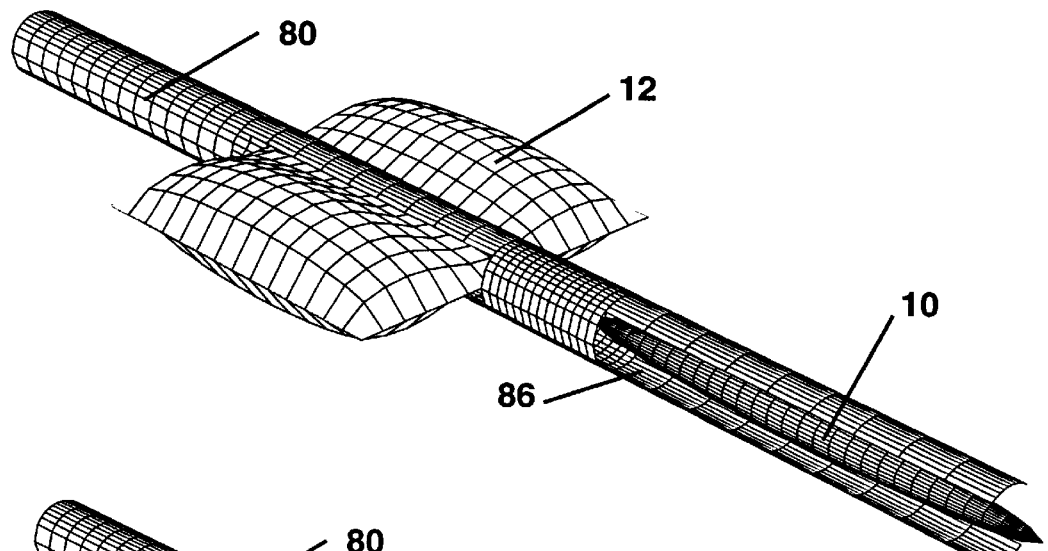
FIG. 19 shows a perspective drawing of the tubular insertion tool with a compressed highly deformable intraocular lens in it.
Figure 20:
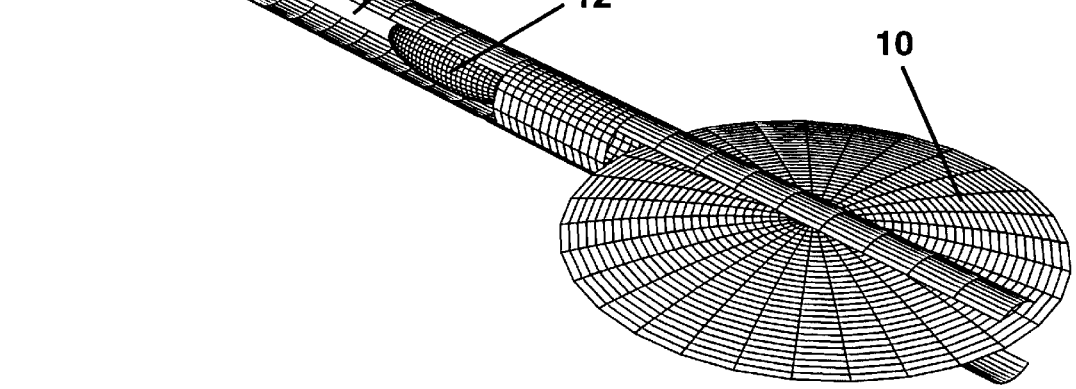
FIG. 20 shows the same as FIG. 19 except that the liquid medium has been shunted back into the optical element so as to make it resume its final shape.

FIG. 19 shows a pre-compressed intraocular lens inside an insertion tool made from a tube 80. FIG. 20 shows the same intraocular lens after the fluid medium has been shunted back into optical element 10 making optical element 10 resume its pre-compression size and shape and substantially reducing the size of bladder 12. For the sake of simplicity, FIGS. 19 and 20 show the insertion tool without plungers 90, spring loaded blades 92 and small openings 84. The main purpose of FIGS. 19 and 20 is to illustrate the relationship between optical element 10, bladder 12, large openings 82, and notches 86.

In FIGS. 16 and 19 bladder 12 is drawn as having a square shape. The exact shape of bladder 12 is not critical for the operation of the highly deformable intraocular lens. For instance, in FIG. 1 bladder 12 has been drawn as having a circular outline.

Figure 21:
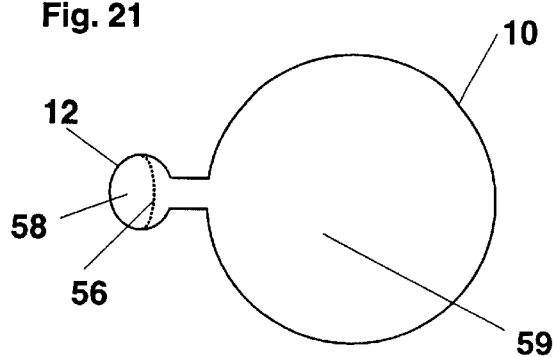
FIG. 21 shows a thin internal membrane creating a small internal compartment inside the bladder.
Figure 22:
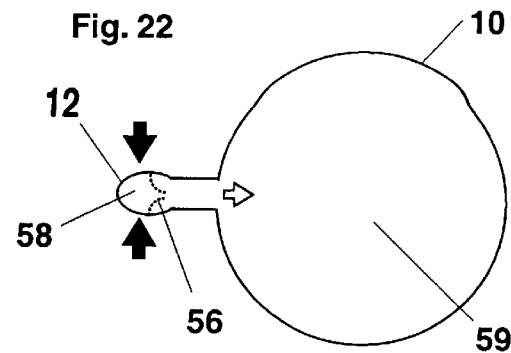
FIG. 22 shows how, by applying outside pressure to the bladder, one may cause the thin internal membrane to rupture so as to empty the contents of the small internal compartment into the major internal space.

FIG. 21 shows how the interior of the highly deformable intraocular lens may be divided into a major internal space 59 and a small internal compartment 58 using an internal membrane 56 inside bladder 12. FIG. 22 shows how one may, by applying external pressure to bladder 12, cause internal membrane 56 to rupture so as to empty the contents of small internal compartment 58 into major internal space 59. The application of external force is indicated with filled arrows and the emptying of the contents of small internal compartment 58 into major internal space 59 is indicated with an open arrow.

Operation

The present invention focuses on the optical element of an intraocular lens and on how to transfer this element through a small corneal incision. In addition to an optical element a conventional intraocular lens comprises one or more haptics. The reason for the emphasis on the optical element in the present invention is that passing of a set of haptics through a small incision is relatively unproblematic. Haptics are typically long, thin, and flexible, and can be bent or straightened so as to have a small cross section. They can therefore be passed relatively easily through a small incision. Optical elements on the other hand are bulky. The insertion of these elements is therefore the main obstacle to the use of very small incisions in cataract surgery.

The basic idea behind the present invention is that of an intraocular lens having optical element 10 filled with a fluid medium of refractive index different from that of the aqueous of the eye and which communicates with external bladder 12 through duct 26. This is arranged so as to allow fluid medium from optical element 10 to be shunted into bladder 12 making optical element 10 very small thereby allowing it to be inserted into an eye through a very small incision. By "very small incision" is here meant an incision which is substantially smaller than the diameter of optical element 10.

The principle of inserting the highly deformable intraocular lens into an eye is illustrated in FIG. 1A through FIG. 1E. FIG. 1A shows the highly deformable intraocular lens in its normal un-deformed state. Most of the fluid medium is in optical element 10 and only a small portion of the fluid medium, if any, is in bladder 12. In FIG. 1B pressure has been applied to squeeze optical element 10 into a narrow shape. The location and direction of the applied pressure is indicated with filled arrows. The reduction in the size of optical element 10 is achieved by shunting the fluid medium from optical element 10 into bladder 12. Bladder 12 is a hollow structure made from an elastic and resilient material. The elasticity allows bladder 12 to expand so as to be able to receive a substantial amount of fluid medium as this is being shunted to it from optical element 10. This is indicated with open arrows in FIG. 1B.

With optical element 10 in the state of reduced volume it is passed through the corneal incision 24. However, bladder 12, which at this point contains most of the fluid medium, remains outside the eye. This is shown in FIG. 1C.

After optical element 10 has been inserted into the eye the fluid medium contained in bladder 12 which up until this point has remained on the outside of the eye is shunted into optical element 12 inside the eye. This is illustrated in FIG. 1D. The open arrows indicate the flow of fluid medium into optical element 10 and the resulting expansion of optical element 10. This restores optical element 10 to its original size and shape. Filled arrows in FIG. 1D indicate external pressure applied to bladder 12 in order to shunt the fluid medium from bladder 12 back into optical element 10. It may be possible to achieve the shunting from bladder 12 to optical element 10 without having to apply external pressure to bladder 12. This can be arranged by having the membrane which forms the outer surface of bladder 12 be resilient so as to exert a force sufficiently strong to propel the fluid medium back into optical element 10 once the external force acting to compress optical element 10 and any obstruction to flow through duct 26 has been removed.

Shunting fluid medium back into optical element 10 causes a reduction in the size of bladder 12. After the size of bladder 12 has been reduced in this manner it is passed through the incision into the eye so as to make both optical element 10 and bladder 12 reside inside the eye. This is shown in FIG. 1E.

The net effect of the procedure illustrated in FIG. 1A through 1E is to move an intraocular lens from the exterior of an eye into the interior of the eye through an opening in the cornea which is substantially smaller than the cross section of optical element 10. That is to say, smaller than the diameter of optical element 10 in its un-compressed state. The details of how one may achieve this are described below.

With regard to the present invention the word "compression" does not mean that the overall volume of the intraocular lens has been reduced. The fluid medium filling the intraocular lens is assumed to be non-compressible. When it is stated that some part of the intraocular lens is "compressed" this means that the volume of this part is reduced by shunting part of the fluid medium normally filling this part to another part of the intraocular lens while leaving the overall volume of the intraocular lens unchanged. Compression of some individual part of the present intraocular lens is therefore in reality a deformation of the overall intraocular lens. For this reason the present intraocular lens is referred to as being highly deformable.

In the preferred embodiment of the present invention optical element 10 is created by two resilient and flexible transparent membranes 18 suspended from a semi-rigid structural ring 16. Structural ring 16 is resilient and flexible enough to be deformed during insertion of the intraocular lens yet has sufficient rigidity to provide structural integrity to optical element 10 and to provide attachment for haptics 20. By having positive pressure inside optical element 10 flexible transparent membranes 18 each take on a spherical shape. Since the fluid medium has a refractive index higher than that of the aqueous this gives optical element 10 the properties of a lens.

In order to be able to control the relative distribution of the fluid medium between optical element 10 and bladder 12 it may be desireable to have valve 28 in duct 26. The principle of this valve is to have a pair of lips 34 come together, as shown in FIG. 7, so as to allow fluid medium to flow in one direction but not in the other. The direction of flow is indicated by an open arrow in FIG. 7. By opening valve 28 fluid medium is free to flow in either direction depending on whether optical element 10 or bladder 12 has the higher internal pressure. In order to open valve 28 external and opposite pressure is applied to struts 36. Pushing struts inward causes lips 34 to buckle so as create open lumen 70. This is illustrated in FIG. 8 in which the pressure applied to struts 36 is indicated with filled arrows.

The direction of valve 28 is optional and depends on whether one wants to limit flow into optical element 10 or out of optical element 10. In case it were desireable to control flow in both directions it would be possible to make valve 28 be bi-directional. This can be accomplished easily by having two valves in series operating in opposite directions.

FIGS. 10 and 11 depict a compression and insertion tool for use with the highly deformable intraocular lens. The compression and insertion tool comprises two blades 40 which are used to compress optical element 10. At the same time as blades 40 compress optical element 10 projections 46 apply pressure onto valve 28 causing it to open so as to allow fluid medium to flow from optical element 10 to bladder 12.

Once compressed as shown in FIG. 11 the part of the compression and insertion tool containing optical element 10 is inserted into the eye through corneal incision 24. The compression and insertion tool is inserted through corneal incision 24 so that the point around which the two parts of the tool pivots, i.e. the location of rivets 50, is aligned with the cornea. While holding the compression and insertion tool in this place the pressure on handles 42 is released and optical element 10 is allowed to regain its original shape and size. In this process fluid medium returns from bladder 12 to optical element 10. Several forces may contribute to propelling fluid medium back into optical element 10: (a) the resilience of optical element 10 makes it restore itself to its pre-compressed shape thereby "sucking" fluid medium from bladder 12, (b) the tensile force exerted by the elastic walls of bladder 12 makes the contents of bladder 12 have higher pressure than the contents of optical element 10, and (c) external pressure may be applied by squeezing bladder 12 using blunt forceps.

Another method for compressing optical element 10 for insertion into the eye is shown in FIGS. 14A through 14F. The basic principle is to push the highly deformable intraocular lens through funnel-shaped insertion tool 64. The first step in this process is to push optical element 10 into funnel shaped insertion tool 64 so as to compress optical element 10 into a narrow elongated shape. This is illustrated in FIGS. 14A to 14C. Compressing optical element 10 causes the fluid medium to be shunted to bladder 12 through duct 26. This is indicated by open arrows in FIG. 14B. The shunting of fluid medium causes bladder 12 to increase in volume. This increase in volume is evident when comparing the size of bladder 12 in FIGS. 14A, 14B and 14C.

Pushing optical element 10 further into funnel shaped insertion tool 64 causes optical element 10 to start to protrude at the other end of funnel shaped insertion tool 64. This can be seen in FIGS. 14C and 14D. At some point in this process optical element 10 will become free of compressing forces. This will allow optical element 10 to start to expand on its own because of the resiliency of structural ring 16.

Once optical element 10 starts to expand, fluid medium begins to flow from bladder 12 back into optical element 10. This flow is indicated with open arrows in FIG. 14E. Further aiding the return of fluid medium to optical element 10 is the compressive effect exerted by funnel-shaped insertion tool 64 on bladder 12 as bladder 12 is being pushed and/or pulled through the narrower sections of funnel-shaped insertion tool 64. That funnel-shaped insertion tool exerts a compressive effect on bladder 12 can be seen in FIGS. 14D and 14E.

In FIG. 14F is shown the highly deformable intraocular lens as it emerges intact and has been reconstituted to its original shape in the inside of the eye after having passed through funnel-shaped insertion tool 64.

It may be desireable to have duct 26 be resilient so that it will be able to stretch during the insertion process. Stretching of duct 26 can be seen in FIGS. 14D and 14E.

As was the case in FIGS. 1A to 1E the net effect of the procedure illustrated in FIGS. 14A to 14F is to transfer an intraocular lens from the outside of the eye to the interior of the eye through an opening which is substantially smaller than the diameter of optical element 10.

The first step in the insertion process as shown in FIGS. 1 and 14 was the shunting of fluid from optical element 10 to bladder 12 in order to reduce the volume of optical element 10. This step could be omitted if the intraocular lens were delivered from the manufacturer with the majority of the fluid medium already in bladder 12. In which case the process could be simplified as it would be possible for the surgeon to only have to pass optical element 10 through the incision, squeeze the fluid from bladder 12 into optical element 10, and then push bladder 12 through the incision in the cornea. A further refinement of this process would be to have the resilient membrane of bladder 17 forming the outer surface of bladder 12 exert a tensile force so as to maintain the contents of bladder 12 under some degree of pressure. In this case valve 28 would serve to control the flow of fluid medium from bladder 12 to optical element 10. With this arrangement all the surgeon would have to do would be to insert optical element 10 through incision 24, open valve 28 so as to make fluid medium flow from bladder 12 into optical element 10, and push bladder 12 through the incision.

A tubular insertion tool for achieving this is illustrated in FIGS. 15 to 20. The tubular insertion tool consists of tube 80 in which have been made two large openings 82, two small openings 84 and two long notches 86 extending inward from the end of tube 80. These openings and notches are shown in FIG. 15.

Large openings 82 allow bladder 12 to expand outward through large opening 82 without being limited by the wall of tube 80. This is shown in FIGS. 16 and 19.

Small openings 84 in tube 80 allow two plungers 90 to be inserted from the outside through the wall of tube 80 in order to make contact with duct 26 and apply pressure so as to open valve 28. This is illustrated in FIGS. 17 and 18. Opening valve 28 causes fluid medium to flow from bladder 12 into optical element 10. The flow is indicated by open arrows in FIG. 18 and the pressure applied by plungers 90 onto valve 28 is indicated with filled arrows. It should be noted that in this embodiment valve 28 is oriented so as to restrict flow from bladder 12 to optical element 10.

Notches 86 in tube 80 are provided to allow optical element 10 to expand as it receives fluid medium from bladder 12. This can be appreciated by comparing FIGS. 19 and 20. In FIG. 19 optical element 10 is compressed into a narrow shape and bladder 12 is distended. Bladder 12 has a square shape in this embodiment. As pointed out above, the exact shape of bladder 12 is not of critical importance. In FIG. 20 the situation is the opposite: bladder 12 is small and optical element 10 is distended. This change is caused by shunting fluid medium from bladder 12 back into optical element 10. The resiliency of structural ring 16 placed in optical element 10 causes optical element 10 to assumes a disk-shaped appearance once it is free to expand. As can be seen in FIG. 20, this expansion makes optical element 10 extend outward from tube 80 through notches 86. Shunting fluid medium to optical element 10 reduces the size of bladder 12 so as to allow it to slide through the inside of tube 80 and into the eye. Similarly, notches 86 allow optical element 10 to slide out of tube 80 and into the intraocular space.

In terms of the insertion process, FIG. 19 depicts the state of the highly compressible intraocular lens as optical element 10 is being inserted into the eye. The transition between the state depicted in FIG. 19 and the one depicted in FIG. 20 takes place with part of the tubular insertion tool inside the eye. The part of the tool which is inside the eye at this time is the section of the tool containing optical element 10 and notches 86. The part of the insertion tool containing bladder 12, large openings 82 and small openings 84 remains outside of the eye.

While maintaining the tubular insertion tool in this position, valve 28 is opened using plungers 90 so as to make fluid medium flow into optical element 10. This causes optical element 10 to expand on the inside of the eye and bladder 12, on the outside of the eye, to contract. After fluid medium has finished flowing into optical element 10 the now diminished bladder 12 is slid down the inside of tube 80 into the eye. This leaves both optical element 10 and bladder 12 inside the eye. The implantation process is then completed by moving the reconstituted highly deformable intraocular lens to the place inside the eye where it is to reside permanently.

While the present invention requires that the fluid medium filling the highly deformable intraocular lens is in a fluid state at the time of insertion through the cornea it may be desireable if this medium were to harden or to become semi-rigid after the intraocular lens has been inserted into the eye. In order to achieve this one may fashion the highly deformable intraocular lens so that it has two internal compartments containing two different fluid media which, when combined, start a polymerization process resulting in an optical material with rigid or semi-rigid consistency. In order to create two separate compartments internal membrane 56 has been placed inside bladder 12 dividing the space inside the highly deformable intraocular lens into small internal compartment 58 and major internal space 59. This is illustrated in FIG. 21.

Internal membrane 56 has been fashioned so that it may be ruptured by applying pressure from the outside onto the part of bladder 12 containing small internal compartment 58. The applied pressure is indicated with filled arrows in FIG. 22. Rupturing of internal membrane 56 causes the contents of small internal compartment 58 to be emptied into major internal space 59. The emptying of small internal compartment 58 brings together the contents of small internal compartment 58 and major internal space 59. This is indicated with an open arrow in FIG. 22.

In order to achieve a thorough blending of the contents of small internal compartment 58 and that of major internal space 59 the fluid medium can be shifted back and forth a number of times between optical element 10 and bladder 12. This can be done using a compression and insertion tool of the kind shown in FIGS. 10 and 11.

The following steps outline the insertion of a highly deformable intraocular lens having a fluid medium capable of undergoing polymerization:

(a) Internal membrane 56 is ruptured by applying pressure on bladder 12 using a forceps or some other blunt tool to squeeze bladder 12.

(b) The contents of small internal compartment 58 and that of major internal space 59 are blended thoroughly by repeatedly shunting the fluid medium back and forth between optical element 10 and bladder 12.

(c) Most of the fluid medium is shunted into bladder 12.

(d) Optical element 10 is inserted into the eye through corneal incision 24.

(e) Fluid medium is shunted from bladder 12 into optical element 10.

(f) Bladder 12 is transferred into the eye.

(g) The highly deformable intraocular lens is moved into its permanent position inside the eye and is left there allowing polymerization to take place.

Summary, Ramification and Scope

The present invention is of an intraocular lens which can be substantially deformed so as to allow it be introduced into an eye through a small incision. The principle of the highly deformable intraocular lens is to have a resilient and flexible fluid-filled optical element and a separate flexible and resilient bladder. In order to reduce the volume of the optical element the fluid is shunted from the optical element to the bladder. After the optical element has been introduced into the eye the fluid is shunted back into the optical element. This reduces the size of the bladder and makes it possible for it to be inserted into the eye through the same small incision.

The main advantage of the highly deformable intraocular lens is to be able to introduce it into an eye through a small incision. In addition this intraocular lens has the following advantages.

* the implantation of the intraocular lens is relatively simple; and
* the highly deformable intraocular lens can easily been made to operate with a fluid medium which will polymerize after implantation in the eye.

Although the description above contains many specificities, these should not be construed as limiting the scope of the invention but as merely providing illustrations of some of the presently preferred embodiments of this invention. The scope of the invention should be determined by the appended claims and their legal equivalents, rather than by the examples given.

I claim:

1. A method for inserting an intraocular lens system into an eye through a small incision, said method comprising:
    (a) providing an intraocular lens system including an optical element made from a flexible and resilient membrane in such a manner so as to form an internal cavity inside said optical element, a flexible and resilient bladder, a fluid optical medium occupying said cavity and said bladder, and means for fluid communication between said internal cavity in said optical element and said bladder;
    (b) inserting said optical element through said small incision;
    (c) while maintaining said bladder on the outside of said eye shunting said fluid optical medium from said bladder to said cavity of said optical element thereby increasing the size of said optical element while reducing the size of said bladder; and
    (d) inserting said bladder through said small incision; whereby the whole of said intraocular lens system has been inserted into the eye through said small incision.

2. The method described in claim 1 in which a resilient structural ring has been attached to said optical element.

3. The method described in claim 1 in which said fluid optical medium undergoes polymerization after said lens system has been inserted into an eye.

4. The method described in claim 1 in which said bladder contains an internal membrane dividing the internal space of said bladder into two separate compartments.

5. A method for inserting an intraocular lens into an eye through a small opening, said method comprising:
    (a) providing said intraocular lens comprising:
        an optical element made out of a transparent and flexible membrane forming a substantially enclosed, collapsible sac; at least one flexible and inflatable bladder; a fluid transparent medium; and means for redistributing a substantial portion of said fluid transparent medium between the interior of said optical element and the interior of said bladder so as to substantially alter the relative sizes of said optical element and said bladder;
    (b) with a substantial portion of said fluid transparent medium contained in said bladder inserting said optical element through said small opening;
    (c) shunting an amount of said fluid transparent medium from said bladder into said optical element so as to substantially increase the size of said optical element; and
    (d) inserting said bladder through said small opening.

6. The method described in claim 5 in which a resilient structural ring has been attached to said optical element.

7. The method described in claim 5 in which the structural property of said fluid transparent medium is altered after said intraocular lens has been inserted into an eye.

8. The method described in claim 5 in which said fluid transparent medium undergoes polymerization after said intraocular lens has been inserted into an eye.

9. An intraocular lens for insertion into an eye following removal of the biological lens, said intraocular lens being capable of being introduced into an eye through a small incision, said intraocular lens comprising:
    (a) an optical element made out of a transparent and flexible membrane forming a substantially enclosed, collapsible sac;
    (b) at least one flexible and inflatable bladder;
    (c) a fluid transparent medium occupying the interior of said optical element and the interior of said bladder; and
    (d) means for allowing a substantial portion of said fluid transparent medium to flow from the interior of said optical element to the interior of said bladder so as to substantially reduce the volume of said optical element in response to pressure applied to the exterior of said optical element.

10. An intraocular lens system as described in claim 9 in which a resilient structural ring has been attached to said optical element.

11. An intraocular lens system as described in claim 9 in which said fluid transparent medium undergoes polymerization after said intraocular lens has been inserted into an eye.

12. An intraocular lens as described in claim 9 in which said bladder contains an internal membrane dividing the internal space of said bladder into two separate compartments.

13. An intraocular lens as described in claim 9, in which said optical element has been inserted into an eye through a small opening after the size of said optical element has been reduced by moving a portion of said fluid medium into said bladder.

* * * * *